US012307671B2

(12) United States Patent
McAlindon et al.

(10) Patent No.: US 12,307,671 B2
(45) Date of Patent: May 20, 2025

(54) OBJECTIVE ASSESSMENT OF JOINT DAMAGE

(71) Applicants: Tufts Medical Center, Inc., Boston, MA (US); Trustees of Boston University, Boston, MA (US)

(72) Inventors: Timothy McAlindon, Arlington, MA (US); Jeffrey B. Driban, Arlington, MA (US); Lori Lyn Price, Winchester, MA (US); Michael Lavalley, Arlington, MA (US); Ming Zhang, Westford, MA (US)

(73) Assignees: Tufts Medical Center, Inc., Boston, MA (US); Trustees of Boston University, Boston, MA (US)

( * ) Notice: Subject to any disclaimer, the term of this patent is extended or adjusted under 35 U.S.C. 154(b) by 685 days.

(21) Appl. No.: 17/609,226

(22) PCT Filed: May 7, 2020

(86) PCT No.: PCT/US2020/031763
§ 371 (c)(1),
(2) Date: Nov. 5, 2021

(87) PCT Pub. No.: WO2020/227463
PCT Pub. Date: Nov. 12, 2020

(65) Prior Publication Data
US 2022/0202356 A1 Jun. 30, 2022

Related U.S. Application Data

(60) Provisional application No. 62/844,418, filed on May 7, 2019.

(51) Int. Cl.
*G06T 7/00* (2017.01)

(52) U.S. Cl.
CPC .. *G06T 7/0016* (2013.01); *G06T 2207/20076* (2013.01); *G06T 2207/30004* (2013.01); *G06T 2207/30096* (2013.01)

(58) Field of Classification Search
CPC .................................................. G06T 7/0016
See application file for complete search history.

(56) References Cited

U.S. PATENT DOCUMENTS

2006/0062448 A1 3/2006 Hirsch et al.
2007/0203430 A1* 8/2007 Lang .................... A61B 5/4514
600/587

(Continued)

OTHER PUBLICATIONS

Nikolaus A Streich et al. "Biochemical Markers in the Diagnosis of Chondral Defects Following Anterior Cruciate Ligament Insufficiency", International Orthopaedics, Springer Berlin, DE, vol. 35, No. 11, Jan. 11, 2011, p. 1633-1637.

(Continued)

*Primary Examiner* — Kevin Ky
(74) *Attorney, Agent, or Firm* — Occhiuti & Rohlicek LLP

(57) ABSTRACT

Determining a composite score includes deriving, based on an image set that includes at least one three-dimensional image of the synovial joint, first and second information. The first information indicates cumulative damage to the synovial joint. The second information indicates either one or both joint pain and loss of function of the synovial joint. The resulting composite score provides an objective measure of joint damage or an extent of joint disease.

20 Claims, 2 Drawing Sheets

(56) References Cited

U.S. PATENT DOCUMENTS

| | | | |
|---|---|---|---|
| 2016/0267234 A1* | 9/2016 | Cooke | G06T 7/0012 |
| 2022/0202356 A1* | 6/2022 | McAlindon | A61B 5/1073 |
| 2024/0148421 A1* | 5/2024 | Kent | A61B 17/72 |
| 2024/0293545 A1* | 9/2024 | Montell | C12N 5/0645 |

OTHER PUBLICATIONS

International Search Report and Written Opinion, PCT Application No. PCT/US2020/031763, mailed Jul. 20, 2020 (13 pages).

Thengade Anita et al. "Image Segmentation for Detection of Knee Cartilage", 2018 Fourth International Conference on Computing Communication Control and Automation (ICCUBEA), IEEE, Aug. 16, 2018, p. 1-5.

\* cited by examiner

OBJECTIVE ASSESSMENT OF JOINT DAMAGE

CROSS-REFERENCE TO RELATED APPLICATIONS

This application is a 371 application of International Application No. PCT/US2020/031763 filed May 7, 2020, which claims the benefit of the May 7, 2019 priority date of U.S. Provisional Application 62/844,418, the content of which is herein incorporated by reference.

STATEMENT AS TO FEDERALLY SPONSORED RESEARCH

This invention was made with government support under grant AR067168 awarded by the National Institutes of Health. The government has certain rights in the invention.

FIELD OF INVENTION

The invention relates to objectively assessing joint damage and in particular, to extracting one or more damage metrics from physical observation of features in and around a joint and a method for combining these into unified quantitative scores reflecting the nature of the osteoarthritis in that joint.

BACKGROUND

Osteoarthritis is a leading cause of pain and disability in the population. In fact, it is the most frequent reason for joint replacement.

Although there are many proposed forms of therapy for alleviating the discomfort of osteoarthritis, many of these require regulatory approval. Among the factors considered in regulatory approval is the efficacy of the proposed therapy to modify disease progression. There are no approved disease-modifying therapies for osteoarthritis.

In the context of osteoarthritis, barriers to developing effective interventions include the inability to identify and thus enrich study samples with people likely to progress; absence of standard definitions of disease progression; absence of structural endpoints that reliably predict reduced pain, improved function, or time to end-stage disease.

It is known to use radiography to observe such features as tibiofemoral joint-space width. However, the use of these observations is hindered by an inability to image soft-tissue structures, unreliability, low sensitivity to change, imprecision, and flawed internal and construct validity. As a result, radiographic observations require large sample sizes and prolonged observation periods to detect a treatment effect.

Magnetic-resonance imaging provides an opportunity to make 3-dimensional quantitative measurements of multiple pathological features that are relevant to osteoarthritis structural progression. But magnetic-resonance imaging also poses technological challenges. Semi-quantitative knee magnetic-resonance-based severity scales are relatively insensitive to change and fail to yield a composite score that represents the whole joint. Quantitative measurements of cartilage segments are burdensome and focus on a single structure instead of assessing osteoarthritis as a multi-factorial disease affecting the whole joint.

SUMMARY

The methods and systems described herein provide a way to assess damage and processes in the whole joint and to assess the effectiveness of various treatments for joint damage using a composite score that is based on various observable features of the joint. This is achieved, in part, by computing a composite score that reflects osteoarthritis damage and processes in the whole joint.

In the embodiments and practices described herein, the particular joint is the knee and the damage is that caused by knee osteoarthritis. The composite scores for this case are referred to herein as the "quantitative composite-knee scores." These composite scores reflect the progression of knee osteoarthritis. As a result, they are useful, for example, as biomarkers for predicting future progression of the disease and for identifying those who are likely candidates for knee replacement. The composite scores are obtained using various biomarkers, and in particular, by carrying out magnetic resonance measurements of cartilage, bone-marrow lesion volumes, and effusion-synovitis volume.

The invention relies on a paradigm shift from conceptualizing knee-osteoarthritis as a disease of articular cartilage to a multi-tissue failure of diarthrodial joints as well as on the recognition of other processes that are of clinical relevance and that relate to symptoms of knee osteoarthritis and structural progression of the disease.

As one example, bone-marrow lesions are frequently evident in knee osteoarthritis. These lesions reflect altered peri-articular bone morphology and density. Thus, there exists an association between such lesions and cartilage damage. Bone-marrow lesions are also associated with knee pain. In addition, bone-marrow lesions predict changes in knee pain and subsequent cartilage loss. Bone-marrow lesions may be responsive to clinical intervention and as a therapeutic target for knee-osteoarthritis disease modification studies.

Another feature that is common in knee osteoarthritis and is strongly associated with pain and with cartilage loss is synovial effusion. Although the association is not completely understood, it is believed to arise at least in part from such factors as biomechanical aspects and inflammatory processes in the synovium.

Combining the measurement of features into composite scores has the potential to provide greater prognostic performance of disease progression, sensitivity to change and discriminative validity. The clinical relevance of cartilage loss, bone-marrow lesions and effusion-synovitis, together with the availability of validated and parsimonious approaches to their measurement on magnetic-resonance images, makes them good choices for inclusion in a composite scoring-system.

In one aspect, the invention features a method that includes determining a composite score that provides an objective evaluation of overall severity of a disease of a synovial joint. Such a method includes receiving an image set that includes at least one image of the synovial joint. The method continues with deriving first and second information based on this image set. The first information is information that is indicative of cumulative damage to the synovial joint. The second information, on the other hand, is indicative of either joint pain or loss of function of the synovial joint. The method continues with determining the composite score based at least in part on the first and second information. This composite score is an objective measure of overall severity of the synovial joint disease.

In some practices, the first information includes a cumulative damage score. Among these practices are those in which this score is determined by obtaining measures of articular cartilage damage at pre-specified locations, which are referred to herein as "informative locations." These informative locations are distributed across medial and lateral distal femur, proximal tibia, and patella and localized using three-dimensional cartilage mapping.

In some practices, the first information includes information about cumulative damage to the joint. Among these practices are those in which it is indicative of radiographic disease progression. Yet others of these practices include those in which the cumulative damage is predictive of disease progression and those in which the cumulative damage is indicative of a likelihood of future joint replacement. Accordingly, such information is useful for enriching clinical trials.

In other practices, the second information includes a disease-activity score. Among these practices are those in which the disease-activity score is calculated from one or more standardized measures of bone marrow lesion volumes and a measured effusion-synovitis volume and those in which the disease-activity score is indicative of a volume occupied by bone-marrow lesions and a volume occupied by effusion resulting from synovitis. In yet other practices, the second information includes information indicative of changes in pain experienced by the subject as a result of joint disease and information indicative of loss of function in the joint.

The method is applicable to any synovial joint, such as the elbow, the shoulder, the hip, and the knee.

In those practices in which the joint is the knee, the feature indicative of damage to cartilage comprises a feature indicative of damage to tibiofemoral cartilage and/or damage to cartilage associated with the patella.

Further practices include those in which receiving the three-dimensional image comprises acquiring a magnetic resonance image of the joint.

Some practices also feature determining progression of joint damage over a period of time. This would be carried out by repeating the determination of the composite scores multiple times during the period.

The method described herein is applicable to joint damage generally and is agnostic to the cause of such damage. However, particular practices include those in which receiving the image set comprises receiving an image set of a joint afflicted with osteoarthritis. Among these are practices in which the joint is a knee.

Among those practices in which the first information indicates cartilage damage are those that further include evaluating a summation of weighted measurements. Each measurement is obtained from an informative location on the joint and weighted based at least in part on the joint's size. In some practices, the first information is a score that indicates cumulative damage and the second information is a score that indicates disease activity. Among the practices are those in which these two scores are added together. Such a sum can be one in which both scores are weighted equally and those in which they are not. The latter includes the case in which the weight assigned to a score is zero.

In other practices, determining a composite score includes weighting parameters that have been derived from the first information and from the second information.

In the foregoing practices, there exist a variety of ways to select the weight to be used for weighting the parameter. These include: selecting the weight based on the subject's age; selecting the weight based on the subject's sex; selecting the weight based on the subject's race; selecting the weight based on the joint's Kellgren-Lawrence grade; selecting the weight based on bone size; and selecting the weight based on the subject's height.

Among other practices of the invention are those that include based at least in part on the composite score, predicting an extent to which structural changes in the joint will progress, predicting an extent to which pain resulting from the disease will progress, predicting an extent to which functional impairment resulting from the disease will progress, predicting a likelihood that the disease will result in a need for replacement of the joint, predicting whether the disease is progressing, and, after having carried out an intervention to ameliorate the disease and, based at least in part on the composite score, determining that the intervention has changed the course of the disease.

In another aspect, the invention features a method that includes: acquiring a first set of images, each of which includes images that correspond to a location of cartilage within a joint; using the first set of images to determine a cartilage-damage index for each of the locations; determining a cumulative-damage score based on the cartilage-damage index for each of the locations; acquiring a second set of images, the images in the second set being images of either volumes having bone-marrow lesions or volumes affected by effusion from synovitis volumes within the joint, or both; using the second set of images to determine a disease-activity score; and determining a composite score for the joint based on the cumulative damage score and the disease-activity score.

Some practices include predicting progression of a disease of said joint based at least in part on said composite score.

Other practices include those in which, based at least in part on said composite score, predicting a likelihood that joint knee will have to be replaced. This is particularly useful when the joint in question is the knee.

Among the practices of the invention are those that include using the composite score or the either the first or second information as a biomarker, and in particular, as a proxy biomarker that indicates the progression of disease, such as osteoarthritis, in the whole joint. In some cases, the first information is useful as a proxy biomarker to indicate the progression of structural damage in the joint, for example as a result of osteoarthritis. In other cases, the second information is useful as a proxy biomarker to indicate the progression of disease activity in the joint. Both of these are tissue-specific roles.

The composite score, the first information, and the second information can serve as biomarkers separately or in combination. In either case, they are useful as an objective basis for measuring tissue-specific effects of various interventions that may be attempted to ameliorate the disease. This feature is particularly useful for drug development or for evaluating experimental therapies.

As an example, if an intervention is one that targets cartilage, then the first information, and in particular, a cumulative damage score derived therefrom, is particularly useful for observing the effect on the cumulative damage. On the other hand, if the intervention is one directed at inflammation reduction or bone-targeted therapies, the second information, and in particular, a disease-activity score derived therefrom, is particularly useful.

Some practices feature the use of either the composite score or the first or second information as a biomarker in conjunction with other biomarkers, such as biochemical biomarkers, to indicate the overall state of the joint disease.

Among the practices of the method are those that include those in which some combination of composite score and the first and second information serve as biomarker scores, wither single or in combination. Such practices include using these biomarker scores as a basis for deriving decision rules based on the effectiveness of a particular intervention that has been carried out to ameliorate the disease.

Some practices feature the use of the composite score as a clinical endpoint for osteoarthritis progression in the joint. Among these practices are those in which the first information includes a cumulative damage score and the second information includes a disease activity score. Such practices include using the cumulative damage score as a clinical endpoint for accumulated structural damage in the joint or using the disease activity score can be used as a clinical endpoint for disease activity in the joint, and in particular, activity of osteoarthritis. Both of these are tissue-specific roles.

In another aspect, the invention features an apparatus comprising an evaluator that receives images of a joint of a subject, wherein the evaluator comprises a volumetric analyzer and a deterioration analyzer, wherein the volumetric analyzer is configured to extract, from the images, an estimate of volume occupied by certain features that are indicative of the joint's condition, and wherein the deterioration analyzer is configured to extract, from the images, information indicative of physical deterioration of the joint.

Some practices include determining, based at least in part on the composite score, that an overall status of the joint has changed. Among these practices are those in which the overall status of the joint has changed for the better and those in which it has changed for the worse.

Other practices include determining, based at least in part on the composite score, that there has been a change in the extent of the disease's activity. Among these practices are those in which the activity has changed for the better and those in which it has changed for the worse.

Yet other practices include determining, based at least in part on the composite score, that there has been a change in the extent of the cumulative damage. Among these practices are those in which the extent has changed for the better and those in which it has changed for the worse.

In the foregoing methods, all steps are executed in a non-abstract manner using non-abstract components. The method requires, in the course of its execution, consumption of energy and generation of waste heat. The same can be said of the apparatus. This results, in a broad sense, in transformation of matter.

The methods and systems described herein provide circuitry that, when coupled to a magnetic-resonance imaging machine, is integrated into the practical application of generating composite scores that can be used for predicting disease progression to enrich a clinical trial or for recognizing and quantifying certain features that are indicative of severity of joint damage based at least in part on one or more of measures of cartilage, bone-marrow lesion, and effusion-synovitis.

The methods and systems described herein are described in the context of osteoarthritis. However, the principles are not tied to this condition and are applicable to assessing the state of a joint as a result of arthritis generally, including, for example, rheumatoid arthritis, as well as arising from injuries generally, including acute injuries.

Moreover, although the description is in terms of the knee, the various synovial joints have enough in common so that the methods and systems are applicable to other synovial joints.

Applicant, acting as his own lexicographer, hereby defines "non-abstract" as meaning "statutory subject matter as defined by 35 USC 101 and accompanying case law as of the time of filing of this application" and "abstract" as the converse thereof.

It is possible to implement any method or system in both an abstract and non-abstract manner. In the interest of brevity, this description only describes non-abstract implementations. The non-abstract implementations operate in the real world using real data to provide real-world results. In contrast, the abstract implementations, which are not described and not covered by the claims, are carried out in one or more imaginary worlds and provide only imaginary-world results.

Because the disclosure is limited to non-abstract implementations, when properly construed in light of the specification, the claims can only be construed to cover non-abstract implementations. Anyone who construes the claims as covering abstract and hence non-statutory subject matter would therefore not be correctly construing the claims in light of the specification.

The methods and systems described herein are not diagnostic methods that are intended to detect the existence of osteoarthritis. Instead, they are intended to provide an objective basis to predict and measure the extent of osteoarthritis progression; to enrich clinical trial samples; and assess the efficacy of candidate treatment methods, thus achieving the practical result of reliably selecting, from a set of candidate treatments, that treatment that shows the most promise.

The methods and systems described herein are not diagnostic methods since their function is to provide an objective basis for enriching clinical trial samples and evaluating candidate therapies over a large population. In fact, arthritis of synovial joints is painful enough so that diagnosis is the least of one's problems.

The methods and systems described herein are not believed to be based on natural laws. This is because there have been no observations of entities in nature that naturally carry out observations on images and deriving objective indicia of joint damage from those observations.

These and other features will be apparent from the following detailed description and its accompanying figures, in which:

DESCRIPTION

Figure 1:
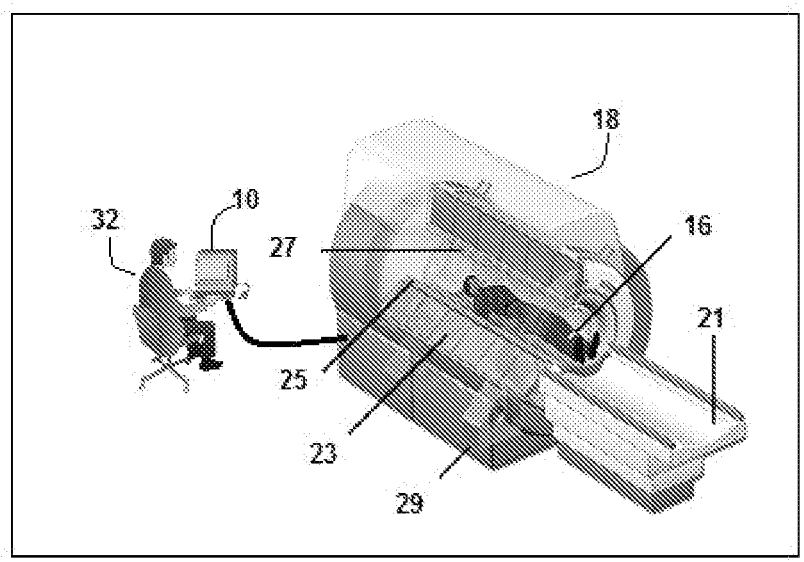
FIG. 1 shows a joint evaluator coupled to an MRI machine.

Referring to FIG. 1, a joint evaluator 10 receives images 12 of a joint of a subject 16 who has been transferred into a magnetic-resonance imaging machine 18 from a patient table 21. The magnetic-resonance imaging machine 18 includes a magnet 23, gradient coils 25, an RF coil 27, and a scanner 29.

Figure 2:
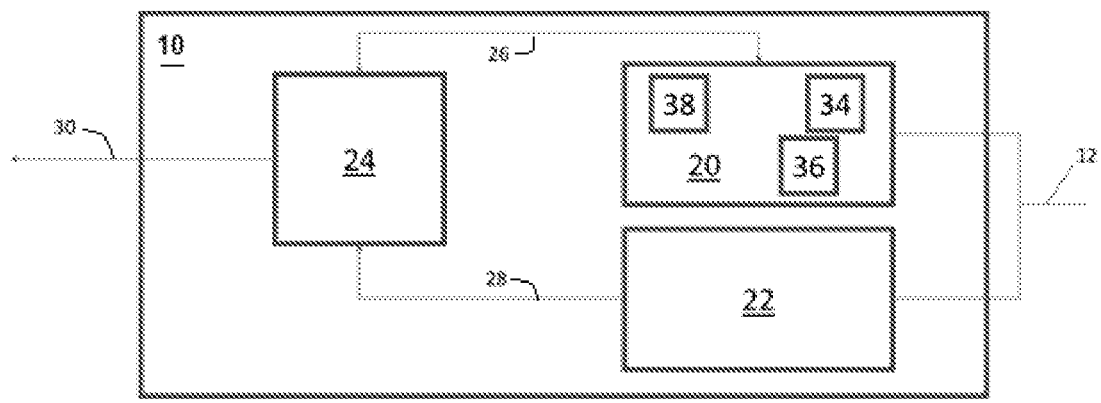
FIG. 2 shows the components of the joint evaluator of FIG. 1.

As shown in FIG. 2, the joint evaluator 10 includes a volumetric analyzer 20 and a deterioration analyzer 22 that each receive the images 12.

The volumetric analyzer 20 extracts, from the images 12, an estimate of the volume occupied by certain features that are indicative of the joint's condition. Examples of suitable volumes include the volume occupied by bone-marrow lesions and the volume affected by effusion resulting from synovitis. A suitable volumetric analyzer 20 is one that uses signal intensity thresholds to delineate various structures of interest and to estimate or measure the volumes of those structures.

The deterioration analyzer 22 extracts, from the images 12, information indicative of physical deterioration of the joint itself. In the case of the knee, the deterioration analyzer 22 outputs an index indicative of cartilage damage in the patella and/or damage to the medial and lateral tibiofemoral cartilage.

A composite-score generator 24 receives one or more deterioration scores 28 from the deterioration analyzer 22 and one or more volumes 26 from the volumetric analyzer 20 and uses them to derive a suitable composite knee score 30.

The operation of the joint evaluator 10 can be understood with reference to a particular application in which the joint evaluator 10 was applied to develop quantitative composite-knee scores using baseline data and data obtained two years later, which was selected from a database maintained by the Osteoarthritis Initiative. The Osteoarthritis Initiative is a multicenter cohort study of subjects 16 who are within the United States and who either already have symptomatic knee osteoarthritis or are at risk of developing it.

The joint evaluator 10 was used to inspect joints of subjects 16 who had had magnetic-resonance readings of their joint assessed as part of a nested case-control study to evaluate longitudinal change and who had already provided baseline data and two-years of longitudinal data for clinical, radiographic, and magnetic-resonance outcomes. A development dataset and a validation dataset were selected via stratified random sampling based on a baseline Kellgren-Lawrence grade and progression within baseline Kellgren-Lawrence strata.

The development dataset was used to evaluate candidate quantitative composite knee-scores 30 and to select a subset of the best-performing composite knee-scores 30 to move onto further testing in the validation dataset.

The validation dataset was used to further validate the quantitative composite knee-scores 30 and select those that had the best discriminative and predictive ability.

In the foregoing study, the deterioration analyzer 22 carried out semi-automated measurements to obtain an index of articular cartilage damage. The volumetric analyzer 20 was used in connection with semi-automated measurements of volumes of bone-marrow lesions and volumes affected by effusion resulting from synovitis. Both the deterioration analyzer 22 and the volumetric analyzer 20 relied on images 12 obtained by a magnetic-resonance imaging machine 18.

The deterioration analyzer 22 derived the cartilage-damage index from measurements made by three-dimensional dual echo steady state imaging with a 140-millimeter field-of-view, 0.7-millimeter thick slices, a zero-millimeter skip, a 25-degree flip angle, an echo time of 4.7 milliseconds, a recovery time of 16.3 milliseconds, and a 307×384 matrix with resolution of 0.365 millimeters along a first direction and a resolution of 0.456 millimeters along a second direction that was perpendicular to the first direction. The total number of slices was 160.

The volumetric analyzer 20 measured bone-marrow lesion and effusion-synovitis volumes by using the intermediate-weighted fat-suppressed imaging sequence with a slightly larger field-of-view and a smaller number of thicker slices. In particular, the volumetric analyzer 20 relied on a field-of-view of 160 millimeters, and three-millimeter thick slices. The volumetric analyzer 20 used images 12 obtained with a zero-millimeter skip, a 180-degree flip angle, an echo time of 30 milliseconds, a recovery time of 3200 milliseconds, and a 313×448 matrix with a resolution of 0.357 millimeters along the first direction and a resolution of 0.511 millimeters along the second direction. The total number of slices was thirty-seven.

The foregoing parameters are only exemplary. It would also have been possible to carry out the method using different parameters.

The deterioration analyzer 22 derived a damage index for the medial and lateral tibiofemoral cartilage. This was carried out by having the deterioration analyzer 22 inspect baseline and 2-year three-dimensional dual-echo steady-state magnetic resonance images 12 using previously validated methods. In doing so, the deterioration analyzer 22 participated in a procedure that included three steps.

In a first step, the deterioration analyzer 22 determined the medial-lateral width of the femur by selecting the medial-most and lateral-most magnetic resonance images 12 that showed bone. This first step relied on a human assistant 32 to mark the most medial and most lateral image that showed bone before the deterioration analyzer 22 could carry out its task.

These images 12 represented minimum and maximum values of the medial-to-lateral axis of the coordinate system, which will be referred to herein as the "y-axis." The deterioration analyzer 22 automatically indicated the slices that contained informative locations in each of the medial and lateral tibiofemoral compartments based on the coordinate system.

A second step also required the human assistant 32. In this step, the assistant 32 manually traced the bone-cartilage boundary using predefined segmentation rules on each of the slices. However, this procedure could also have been carried out semi-automatically.

Following this second step, control was returned to the deterioration analyzer 22 to carry out a third step. In this third step, the deterioration analyzer 22 translated the length of the bone-cartilage boundary to a standardized anterior-to-posterior axis and also identified the informative locations so that the assistant 32 could manually carry out measurements of cartilage thickness at those locations. However, this procedure could also have been carried out semi-automatically.

Once the assistant 32 carried out this procedure, the deterioration analyzer 22 then computed the cartilage damage index. It did so by summing the products of cartilage thickness, cartilage length measured in the anterior to posterior direction, and voxel size from each informative location.

The deterioration analyzer 22 also provided an index that was indicative of damage to the cartilage of the patella. The deterioration analyzer 22 carried this out based on both baseline images and 2-year three-dimensional dual-echo steady-state magnetic resonance images.

The deterioration analyzer 22 determined the medial-lateral width of the patella by receiving, from the human assistant 32, a selection of the medial-most and lateral-most magnetic resonance image slices that included bone. Upon having received the human assistant's selection, the deterioration analyzer 22 then identified the six magnetic resonance images with informative locations, three from each of the medial and lateral facets.

The assistant 32 delineated the bone-cartilage boundary using predefined segmentation rules on each of these slices. However, this procedure could also have been carried out semi-automatically or automatically. Upon completion, control returned to the deterioration analyzer 22, which then translated the length of the bone-cartilage boundary to a standardized superior-to-inferior axis and indicated the pre-defined informative locations.

The assistant 32 then measured the cartilage thickness at those points and provided this information to the deterioration analyzer 22. However, this procedure could also have been carried out semi-automatically or automatically. The deterioration analyzer 22 then computed the index of damage to the patella's cartilage. It did so by summing the products of cartilage thickness, cartilage length in the anterior to posterior direction, and voxel size from each informative location.

The volumetric analyzer 20 was then used to measure the extent of volumes with bone-marrow lesions. These volumes correspond to regions of high-signal intensity within bone on intermediate-weighted fat-saturated magnetic resonance images in the medial and lateral tibiofemoral and patellar compartments.

The volumetric analyzer 20 included both a marker 34 and a filter 36. The marker 34 was configured to mark a region-of-interest. In some cases, the region is that around a bone-marrow lesion. In other cases, the region is that associated with a particular slice. The filter 36 was configured to classify the marked region by comparing a pre-defined threshold with a score derived from an intensity histogram distribution obtained from within the region-of-interest marked by the marker 34.

A follow-up slice used the same threshold as was used in the corresponding baseline slice. Through intervention by the assistant 32, and with the help of dual screens to simultaneously display baseline and follow-up images 12, it was possible to manually adjust the threshold and to remove those regions that did not have bone-marrow lesions.

To promote the assistant's ability to co-locate the corresponding bone-marrow lesions on baseline and follow-up images, it is useful to provide dual screens to simultaneously display baseline and follow-up magnetic-resonance images.

The volumetric analyzer 20 also measured knee effusion-synovitis volume. It did so by having the marker 34 mark the first and last slice of the knee on intermediate-weighted fat-saturated magnetic resonance images as well as the base of the patella (i.e., the proximal border), and the distal attachment of the patellar ligament on a central slice for which the patellar ligament was clearly visible.

A segmentation unit 38 automatically segmented effusion-synovitis based on an existing threshold.

The assistant 32 then performed a quality check of the segmentation unit's work. To do so, the assistant 32 manually adjusted the threshold to change the effusion-synovitis boundaries. Then the assistant 32 reviewed the automatically-generated segmentation results provided by the segmentation unit 38 and removed, from those results, any areas of high signal intensity that clearly did not arise as a result of effusion-synovitis. These included high signal intensity arising from such phenomena as subchondral cysts and blood vessels.

The composite knee-score 30 is a "composite" score because it is derived from multiple factors. Each factor by itself would generally be regarded as insufficient to indicate joint condition by itself. However, when taken together, an unexpected synergy arises with the result that the whole becomes greater than the sum of the parts. By combining these factors in the correct way, the composite knee-score 30 as described herein provide objective and reliable measures of joint condition.

The composite-score generator 24 generated the composite knee-scores 30 based on measurements of articular cartilage damage and on values affected by certain conditions and also on volumes affected by certain conditions.

The measurements of articular cartilage damage comprised measurements in the medial and lateral compartments in the femoral, tibial, and patellar regions.

The measurements of affected volumes included measurements of volumes affected by bone-marrow lesions and measurements of volume affected by effusion resulting from synovitis. The measurements of volumes affected by bone-marrow lesions were made in the medial and lateral compartments in the femur, the tibia, and the patella. The measurement of volume affected by effusion due to synovitis was a single whole-knee measurement.

All magnetic resonance measurements were corrected for knee size based on bone width. Measurements were standardized thereby placing all measurements on the same scale. The difference between the standardized baseline and follow-up measures were used to develop the composite knee-score 30. Cartilage-damage index difference scores were multiplied by −1 to be consistent with the other measures, in which higher values indicate worse disease. In some practices, standardization is carried out by subtracting the baseline mean and dividing by the baselines standard deviation. However, other standardization methods can be used, particularly when the amount of available data is sufficiently large.

A priori, three approaches were identified for developing the quantitative composite-knee score 30: principal components analysis, application of inverse variance weighting to the sum of magnetic resonance measures on the original, unstandardized measures, and calculating an unweighted sum of the standardized change of the thirteen measures. The analyses led to two novel outcome subdomains: an unweighted cumulative damage score calculated by summing the standardized change for each of the six cartilage-damage measurements and an unweighted disease activity score calculated by summing the standardized change in effusion-synovitis volume and the bone-marrow-lesion volumes for the six regions.

The method described herein included intervention by a human assistant 32 to carry out certain steps. In principle, one or more of these steps could also be carried out by a suitably programmed processor.

Figure 3:
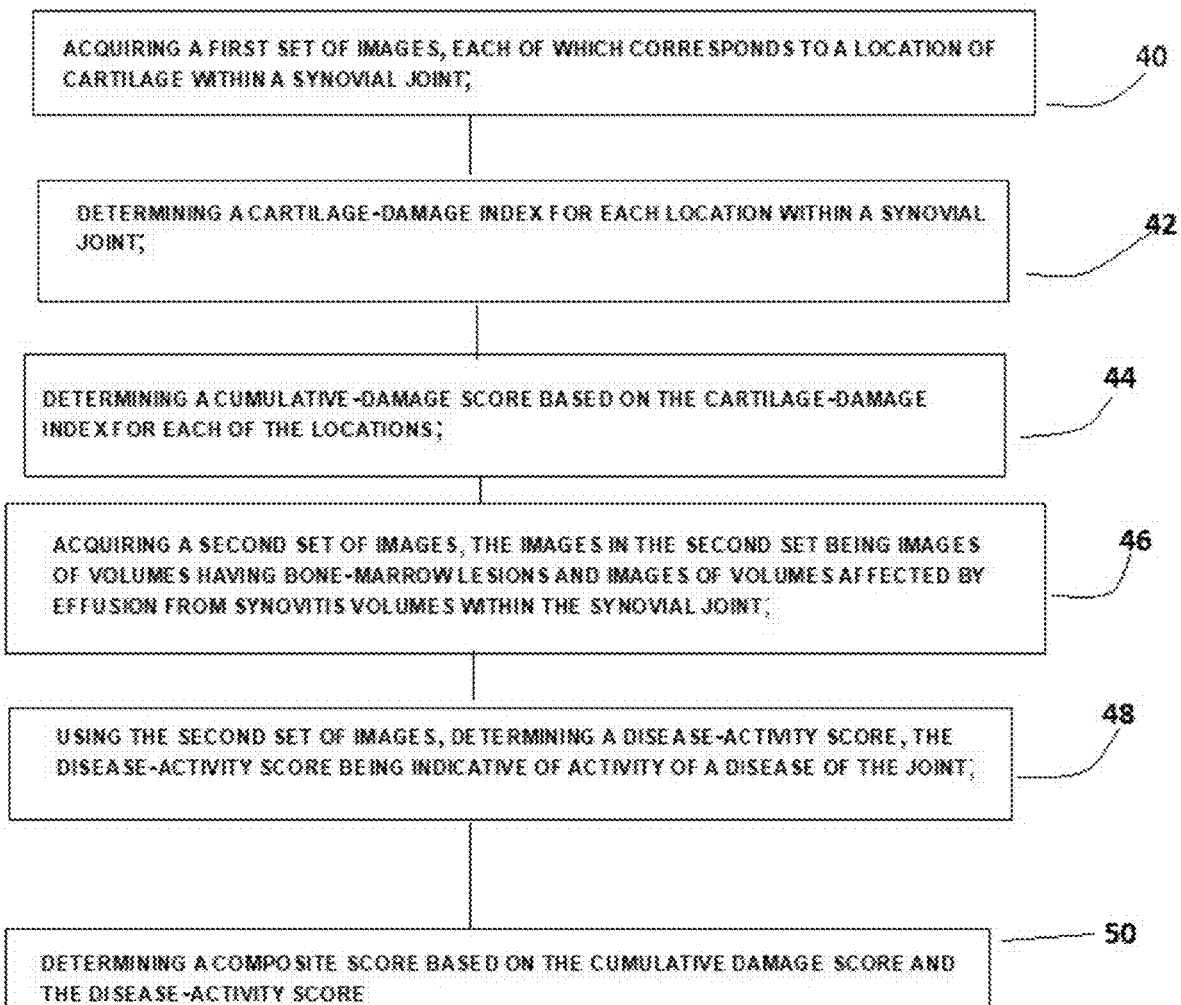
FIG. 3 shows steps carried out by the joint evaluator of FIG. 1.

Referring now to FIG. 3, the apparatus described herein is configured to carry out the step of acquiring a first set of images, each of which corresponds to a location of cartilage within a synovial joint (step 40). This is followed by the step of determining a cartilage-damage index for each location within that synovial joint (step 42) and using the cartilage-damage index thus determined to carry out the step of determining, for each of the locations, a cumulative-damage score based on that cartilage-damage index (step 44). Operation continues with the acquisition of a second set of images, which include images of volumes having bone marrow lesions and images of volumes affected by effusion from synovitis volumes within the synovial joint (step 46). This second set of images is then used to carry out the step of determining a disease-activity score that is indicative of disease activity of the joint (step 48). Having now determined both the cumulative-damage score and the disease-activity score, the apparatus proceeds to carry out the step of determining a composite score based on both the cumulative-damage score and the disease-activity score (step 50).

Having described the invention and a preferred embodiment thereof, what is new and secured by Letters Patent is:

1. A method that is tied to a particular machine and that is also integrated into a practical application that requires use of said particular machine to carry out, the practical application being that of assessing cartilage damage in a joint, the particular machine being a joint evaluator that comprises a magnetic-resonance imaging machine having a magnet, an RF coil, and gradient coils, wherein said method comprises using said particular machine to carry out said practical application by carrying out the steps of:

using said magnetic-resonance imaging machine, exposing a joint to a magnetic field from said magnet and exciting said gradient coils and said RF coil so as to cause acquisition of a first set of images, each of which corresponds to a location of cartilage within a synovial joint;
  using said first set of images, determining a cartilage-damage index for each of said locations;
  determining a cumulative-damage score based on said cartilage-damage index for each of said locations;
  using said magnetic-resonance imaging machine, exposing said joint to said magnetic field from said magnet and exciting said gradient coils and said RF coil so as to cause acquisition of a second set of images, said images in said second set being images of volumes having bone-marrow lesions and images of volumes affected by effusion from synovitis volumes within said synovial joint;
  using said second set of images, determining a disease-activity score, said disease-activity score being indicative of activity of a disease of said joint;
  using said joint evaluator, determining a composite score based on said cumulative damage score and said disease-activity score, and
  using said composite score as a biomarker that indicates progression of said disease of said joint,
  whereby said composite score thus determined is used for predicting disease progression to enrich a clinical trial or for recognizing and quantifying features that are indicative of severity of joint damage.

2. The method of claim 1, further comprising, based at least in part on said composite score, predicting progression of said disease of said joint.

3. The method of claim 1, further comprising determining progression of joint damage over a period of time, wherein determining said progression comprises repeating said determination of said composite score multiple times during said period of time.

4. The method of claim 1, further comprises evaluating a summation of weighted measurements, each of said measurements being obtained at pre-specified informative locations on said synovial joint, wherein said weighted measurements are weighted based at least in part on a size of said synovial joint.

5. The method of claim 1, further comprising enriching a clinical trial based at least in part on said composite score.

6. The method of claim 1, further comprising determining, based at least in part on said composite score, that an overall status of said joint has changed.

7. The method of claim 1, further comprising determining, based at least in part on said composite score, that there has been a change in an extent of activity of said disease.

8. The method of claim 1, further comprising determining, based at least in part on said composite score, that there has been a change in an extent of said cumulative damage.

9. The method of claim 1, further comprising, based at least in part on said composite score, predicting an extent to which structural changes in said joint will progress.

10. The method of claim 1, further comprising, based at least in part on said composite score, predicting an extent to which pain resulting from said disease will progress.

11. The method of claim 1, further comprising, based at least in part on said composite score, predicting an extent to which functional impairment resulting from said disease will progress.

12. The method of claim 1, further comprising, based at least in part on said composite score, predicting a likelihood that said disease will result in a need for replacement of said joint.

13. The method of claim 1, further comprising, based at least in part on said composite score, predicting whether said disease is progressing.

14. The method of claim 1, further comprising carrying out an intervention to ameliorate said disease and using said composite score as a biomarker upon which to base a determination that said intervention has changed the course of said disease.

15. The method of claim 1, wherein determining said composite score comprises weighting either said first set of images or said second set of images.

16. The method of claim 1, wherein said composite score is an objective measure of joint damage.

17. The method of claim 1, wherein said composite score is an objective measure of overall severity of said synovial joint disease.

18. The method of claim 1, wherein determining said cumulative-damage score comprises determining said score based at least in part on damage to tibiofemoral cartilage of a knee and on damage to cartilage associated with a patella of said knee.

19. An apparatus comprising a joint evaluator that comprises a magnetic-resonance imaging machine that acquires first and second sets of images, said first set comprising images corresponding to locations of cartilage within a joint and said second set comprising images of volumes having bone-marrow lesions and images of volumes affected by effusion from synovitis volumes within said joint, said joint being a synovial joint, said joint evaluator further comprising a volumetric analyzer, a deterioration analyzer, and a composite score generator, wherein said volumetric analyzer is configured to use said first set to determine a cartilage-damage index for each of said locations and to determine a cumulative-damage score based on said cartilage-damage index for each of said locations, wherein said deterioration analyzer is configured to determine, from said second set of images, a disease-activity score, said disease-activity score being indicative of activity of a disease of said joint, wherein said composite-score generator derives a composite score based at least in part on said cartilage-damage index and said disease-activity score, wherein said composite score is a biomarker that indicates progression of said disease of said joint, whereby said composite score provides an objective basis for predicting disease progression or for recognizing and quantifying feature that are indicative of severity of joint damage.

20. The method of claim 1, wherein said synovial joint is a knee, said method further comprising, based at least in part on said composite score, predicting a likelihood that said knee will have to be replaced.

* * * * *